(12) United States Patent
Bäck

(10) Patent No.: US 8,992,496 B2
(45) Date of Patent: Mar. 31, 2015

(54) CONVERTIBLE ABSORBENT ARTICLE

(71) Applicant: SCA Hygiene Products AB, Göteborg (SE)

(72) Inventor: Lucas Bäck, Billdal (SE)

(73) Assignee: SCA Hygiene Products AB, Göteborg (SE)

( * ) Notice: Subject to any disclaimer, the term of this patent is extended or adjusted under 35 U.S.C. 154(b) by 232 days.

(21) Appl. No.: 13/782,688

(22) Filed: Mar. 1, 2013

(65) Prior Publication Data

US 2013/0211367 A1  Aug. 15, 2013

Related U.S. Application Data

(63) Continuation of application No. 12/599,134, filed as application No. PCT/SE2007/050392 on May 31, 2007, now Pat. No. 8,430,858.

(51) Int. Cl.
| | |
|---|---|
| *A61F 13/49* | (2006.01) |
| *A61F 13/493* | (2006.01) |
| *A61F 13/496* | (2006.01) |
| *A61F 13/56* | (2006.01) |
| *A61F 13/64* | (2006.01) |
| *A61F 13/15* | (2006.01) |

(52) U.S. Cl.
CPC ............. *A61F 13/565* (2013.01); *A61F 13/64* (2013.01); *A61F 13/15804* (2013.01); *A61F 13/15577* (2013.01)
USPC ...... 604/385.11; 604/386; 604/392; 604/394; 604/395

(58) Field of Classification Search
USPC .............. 604/385.01, 385.11, 385.3, 386, 604/389–395
See application file for complete search history.

(56) References Cited

U.S. PATENT DOCUMENTS

| 5,624,428 A | 4/1997 | Sauer |
|---|---|---|
| H1674 H | 8/1997 | Ames et al. |
| 6,027,484 A | 2/2000 | Romare |

(Continued)

FOREIGN PATENT DOCUMENTS

| DE | 197 32 499 A1 | 2/1999 |
|---|---|---|
| DE | 198 13 334 A1 | 9/1999 |

(Continued)

OTHER PUBLICATIONS

International Search Report for PCT/SE2007/050392, mailed Feb. 6, 2008.

(Continued)

*Primary Examiner* — Tan-Uyen T. Ho
*Assistant Examiner* — Kathryn E Ditmer
(74) *Attorney, Agent, or Firm* — Buchanan Ingersoll & Rooney PC

(57) ABSTRACT

An absorbent article having a waistband which is attached to first and second body portions of the article. The first body portion is attached to the waistband by at least a fastening means wherein the article assumes a pant diaper form. The waistband has a reception surface and a perforation. The perforation allows the reception surface to be separated into first and second belt portions. At least a part of the reception surface is located on each belt portion, thereby allowing the article to assume a belt diaper form. The first belt portion comprises at least one fastening means. The second fastening means is arranged so that the absorbent article can be readily converted from a pant diaper form to a belt diaper form.

8 Claims, 9 Drawing Sheets

(56) References Cited

U.S. PATENT DOCUMENTS

| | | |
|---|---|---|
| 6,342,050 B1 | 1/2002 | Rönnberg et al. |
| 6,743,321 B2 | 6/2004 | Guralski et al. |
| 2002/0151858 A1 | 10/2002 | Karami et al. |
| 2002/0193776 A1 | 12/2002 | Fernfors |
| 2003/0135192 A1 | 7/2003 | Guralski et al. |
| 2004/0108043 A1 | 6/2004 | Otsubo |
| 2005/0143709 A1 | 6/2005 | Lindstrom |
| 2006/0004339 A1 | 1/2006 | Lord et al. |
| 2006/0052763 A1 | 3/2006 | Tachibana |
| 2006/0116654 A1 | 6/2006 | Kondo |
| 2007/0049897 A1 | 3/2007 | LaVon et al. |
| 2007/0245447 A1 | 10/2007 | Fujioka |
| 2008/0021425 A1* | 1/2008 | Nakaoka et al. ............ 604/365 |
| 2008/0091163 A1 | 4/2008 | Fujioka |
| 2008/0319412 A1 | 12/2008 | Lornell |

FOREIGN PATENT DOCUMENTS

| | | |
|---|---|---|
| EP | 0 605 012 | 7/1994 |
| EP | 1 035 818 B1 | 4/2002 |
| EP | 1 523 968 A1 | 4/2005 |
| EP | 1 559 387 A1 | 8/2005 |
| FR | 2 586 558 | 3/1987 |
| JP | 08-510145 A | 10/1996 |
| JP | 2003-175066 A | 6/2003 |
| JP | 2005-021196 A | 1/2005 |
| JP | 2005-527250 A | 9/2005 |
| JP | 2005-270359 A | 10/2005 |
| WO | WO 95/19753 A1 | 7/1995 |
| WO | WO 2005/060912 A1 | 7/2005 |
| WO | WO 2005/089690 A1 | 9/2005 |
| WO | WO 2006/019049 A1 | 2/2006 |
| WO | WO 2006/068563 A1 | 6/2006 |
| WO | WO 2006/123976 A1 | 11/2006 |
| WO | WO 2007/024928 A1 | 3/2007 |
| WO | WO 2007/071267 A1 | 6/2007 |

OTHER PUBLICATIONS

Written Opinion of the International Searching Authority for PCT/SE2007/050392, mailed Feb. 6, 2008.

Decision on Grant dated Oct. 26, 2010, issued in the corresponding Russian Patent Application No. 2009149702, and an English Translation thereof.

An English Translation of the Office Action (Notice of Reasons for Rejection) dated Jan. 17, 2012, issued in the corresponding Japanese Patent Application No. 2010-510255. (4 pages).

* cited by examiner

CONVERTIBLE ABSORBENT ARTICLE

This application is a Continuation of application Ser. No. 12/599,134 filed on Nov. 6, 2009 now U.S. Pat. No. 8430585, which is a National Stage of PCT/SE2007/050392, filed on May 31, 2007. The disclosure of the prior applications is hereby incorporated by reference herein in their entirety.

TECHNICAL FIELD

The present invention describes absorbent articles which are intended for uptake and control of bodily exudates, e.g. urine, menses and faeces. More specifically, the present invention relates to an absorbent article which can assume more than one form, and which a user can readily adapt according to their wishes. The invention also relates to a method for manufacturing such articles.

BACKGROUND OF THE INVENTION

To meet increasing demand for flexibility in the field of disposable absorbent hygiene articles, absorbent articles which can assume more than one form have been produced. In this way, the user can choose the form and the method of application for the article which they find most suitable.

Pant diapers are designed so that their appearance and function mirrors that of pant-type underwear. Pant diapers have a front portion which—when the diaper is worn—is located against the stomach of the wearer, a rear portion which is located against the lower back/buttocks of the wearer and a crotch portion which is located between the wearer's legs. The front and rear portions form a waist opening and two leg openings. The waist opening may be defined by a waistband which encircles the waist of the wearer. Pant diapers are applied to a wearer by being pulled up the legs, over the buttocks and hips and up to the waist, in the same way as normal underwear. They may be removed by reversing this action, or by opening or tearing the diaper between the waist opening and one or more leg openings. Examples of pant diapers are training pants for infants and incontinence pants for adults.

Belt diapers comprise a front portion which is intended to be worn against the stomach of the wearer, a rear portion which is intended to be worn against the lower back/buttocks of the wearer and a crotch portion which is intended to be worn between the wearer's legs. Belt diapers further comprise a belt, which usually comprises a pair of belt portions, said belt being joined to the front or the rear portion. The belt is long enough to encircle the waist of the wearer, often in combination with the front or rear portion to which it is joined. Typically for a belt diaper, at least a portion of the waist region of the diaper consists solely of the belt. To apply a belt diaper, the belt is first fastened around the wearer's waist, leaving the remainder of the diaper hanging freely. The diaper is then pulled through the legs of the wearer, so that the crotch portion is located between the wearer's legs, and fastened to the belt on the other side of the wearer (most commonly on the outside of the belt). Suitable fastening means are arranged to close the belt around the wearer's waist, and on the front or rear portions to fasten the remainder of the diaper to the belt in its correct conformation. A diaper having this form can be easily changed by the wearer themselves, and it is possible to change the diaper while the wearer is standing up.

WO 05/089690 discloses a pant diaper which can function as a belt diaper by breaking the belt in two places. The resulting belt portions can be closed around the waist of the wearer, and the body of the diaper fastened to the belt portions. However, the fact that two perforations are present, one on each lateral edge of the front portion means that, in the belt diaper form, the combined length of the two belt portions is much shorter than the length of the waistband of the pant diaper. In effect, a length corresponding to the extension of the front portion is lost when converting from the pant diaper to belt diaper form. The article of WO 05/089690 therefore has a limited range of fit and adjustability.

EP 1 559 387 discloses a pant diaper which can be torn open at the belt portions and then closed again. It can therefore be opened in urgent situations and temporarily re-fastened.

Similarly, US2006/0116654 discloses a pant diaper which can be opened and re-sealed at the crotch.

U.S. Pat. No. 5,624,428 discloses a traditional diaper having two fastening means, one of which is located on an outwardly-folded section of the waistband. In normal use, both fastening means are engaged. Releasing the second fastening means expands the waist region, allowing the diaper to be pulled down like a pair of pants.

WO 2006/019049 describes a combined pant/traditional diaper. The diaper can be opened at break sections, so can be used as a traditional diaper. A belt-diaper is not disclosed.

US 2005/0143709, EP 1 523 968 and WO 2006/068563 disclose fastening means which are covered or folded in some way. These documents do not concern combined belt-pant products.

Despite the activity in the field, there remains a need for an absorbent article, such as a diaper, which can assume more than one form, and which a user can readily adapt according to their wishes. Furthermore, it is desirable that the absorbent article is packaged ready for use in one form and can be readily converted into another form. Absorbent articles which can assume more than one form also provide a greater range of fit, allowing the same product to be used on wearers of different waist sizes.

SUMMARY OF THE INVENTION

The present invention provides an absorbent article comprising a first body portion, a second body portion and a crotch portion located between said first and second body portions in the longitudinal direction (L) of the article. The article comprises a waistband which is attached to the first and second body portion of the article such that the lateral edges of the first and second body portions are interconnected by said waistband. In such a way, the article assumes a pant diaper form (A) in which the waistband forms part of the waist portion of the pant diaper.

The waistband comprises a reception surface for a fastening means. The waistband also comprises at least one perforation extending across the waistband which allows the waistband to be separated into first and second belt portions. This allows the pant diaper to be converted into a belt diaper, whereby at least a part of the reception surface is located on each belt portion. The perforation also allows easy removal of a pant diaper when soiled, which occurs by breaking the waistband at the perforation. This avoids the need for pulling the soiled pant diaper down the legs of the wearer, and the associated risks of leakage of faeces or soiling the legs of the wearer.

The first belt portion comprises at least one first fastening means adapted to be attached to the reception surface on the second belt portion. The first body portion of the article comprises at least one second fastening means which is adapted to be attached to the reception surface on the first and/or second belt portion such that the article assumes a belt diaper form.

The at least one second fastening means is arranged such that, in the pant diaper form (A), the first body portion is releasably attached to the reception surface of the waistband via said at least one second fastening means.

Suitably, the reception surface is arranged on the garment-facing side of the waistband. Preferably, the reception surface constitutes the garment-facing surface of the waistband.

In an article according to the invention, the first and second fastening means may comprise hook material of a hook-and-loop type fastener and the reception surface comprises loop material of a hook-and-loop type fastener. Alternatively, the first and second fastening means may comprise adhesive fastening means and the reception surface may comprise reception surface for said adhesive fastening means. Preferably, the second fastening means is arranged on the wearer-facing side of the first body portion.

The perforation is suitably located adjacent or aligned with the longitudinal centre line of the first body portion in the pant diaper form (A). The second fastening means is preferably arranged on the wearer-facing side of the first body portion.

Furthermore, the first fastening means may be arranged to face away from the wearer when the article assumes the pant diaper form (A), and is arranged to face towards the wearer when the article assumes the belt diaper form (B). The first fastening means may be located on a foldable flap which is arranged such that, in the pant diaper form (A), the first fastening means is arranged to face away from the wearer, wherein the flap can be folded such that, in the belt diaper form (B), the first fastening means is arranged to face towards the wearer.

Suitably, the first fastening means is located adjacent to the free end of the first belt portion formed upon separating the waistband. The perforation is suitably located adjacent or aligned with the longitudinal centre line of the first body portion in the pant diaper form (A). The waistband may have elastic properties in at least one region thereof.

The invention also relates to a method for manufacturing the absorbent articles described herein, said method comprising the steps of:
a. providing first and second continuous parallel webs of waistband material; at least the first web of waistband material comprising a reception surface for a fastening means, the first web of waistband material being provided with perforations at a predetermined spacing in at least a portion of the first web in which reception surface is present; the first web of waistband material further comprising first fastening means at the same predetermined spacing;
b. providing chassis elements having a first body portion, a second body portion and a crotch portion; said chassis elements further comprising at least one second fastening means on the first body portion;
c. placing the chassis elements on the webs of waistband material at the predetermined spacing, so that the at least second fastening means on the first body portion of each chassis element overlaps with the first web of waistband material, and second body portion of each chassis element overlaps with the second web of waistband material;
d. attaching the second fastening means of the first body portion to the first web of waistband material; and attaching the rear body portion of each chassis element to the second web of waistband material;
e. folding each chassis element in the crotch portion such that the first and second webs of waistband material are brought into contact in the region between the chassis elements;
f. joining the first and second webs of waistband material to each other at the predetermined spacing, in the region between the chassis elements;
g. cutting the first and second webs of waistband material at the predetermined spacing in such a way that the first and second webs of waistband material remain joined to each other on both sides of each cut, and in such a way that the length of waistband material between each cut includes a chassis element, a perforation and a first fastening means;

so as to provide individual absorbent articles.

Definitions

As used herein, a "perforation" is used to describe a region of the waistband which is weakened in some way so that the waistband can be separated into two belt portions. Preferably, the waistband is weakened sufficiently that separation of the waistband can be carried out manually (e.g. by tearing the belt) but is not so weak that the waistband separates into two belt portions unintentionally (e.g. when pulled up over the hips of the wearer in the pant diaper form). The perforation suitably comprises a series of through-holes in the waistband, although blind-holes may also be used. If the waistband comprises more than one layer of material, perforations may be through-holes in one or more layers and blind-holes in one or more other layers, with further layers being non-perforated. Additionally, the perforation can be introduced by laying an intermediate piece over a fold in the waistband and cutting the waistband at the fold so that the intermediate piece holds the waistband together. The intermediate piece is removably fastened to the waistband, so that its removal separates the waistband into two belt portions. The nature of the perforation depends primarily upon the materials which constitute the waistband, and may—for instance—be introduced mechanically, thermally or using ultrasound.

The term "absorbent article" refers to products that are placed against the skin of the wearer to absorb and contain body exudates, like urine, faeces and menstrual fluid. The invention mainly concerns disposable absorbent articles, which means articles that are not intended to be laundered or otherwise restored or reused as an absorbent article after the first use.

BRIEF DESCRIPTION OF THE DRAWINGS

The invention will be described with reference to the enclosed Figures, in which:

FIG. 6 illustrates a process which may be used to manufacture the absorbent articles of the invention.

DETAILED DESCRIPTION OF PREFERRED EMBODIMENTS

Figure 1A:
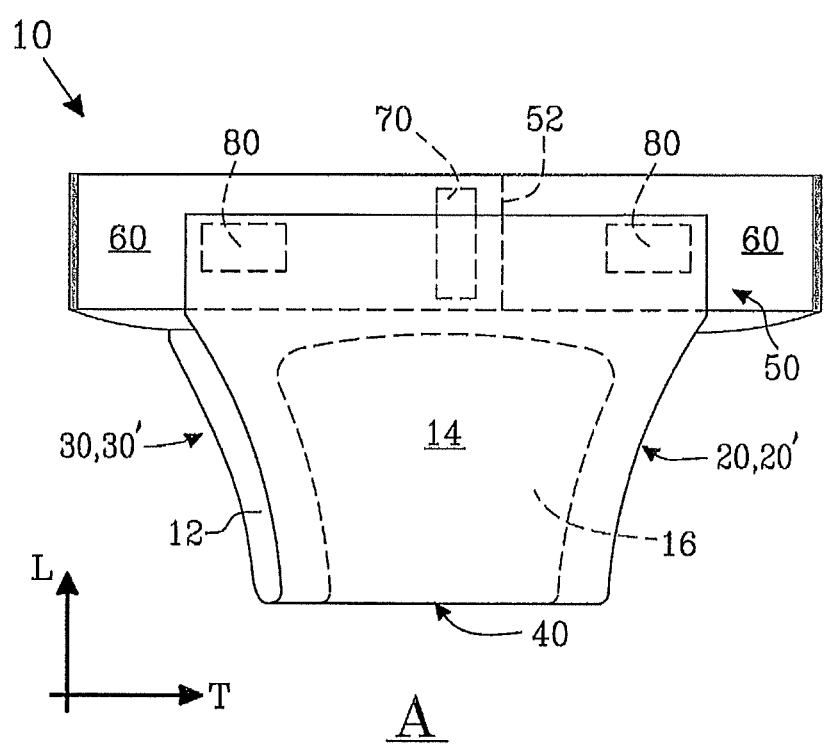
FIGS. 1A-1E illustrate the sequence of actions required to convert an absorbent article of the invention from the pant diaper form (FIG. 1A) to the belt diaper form (FIG. 1C) and apply it (FIG. 1E).
Figure 1B:
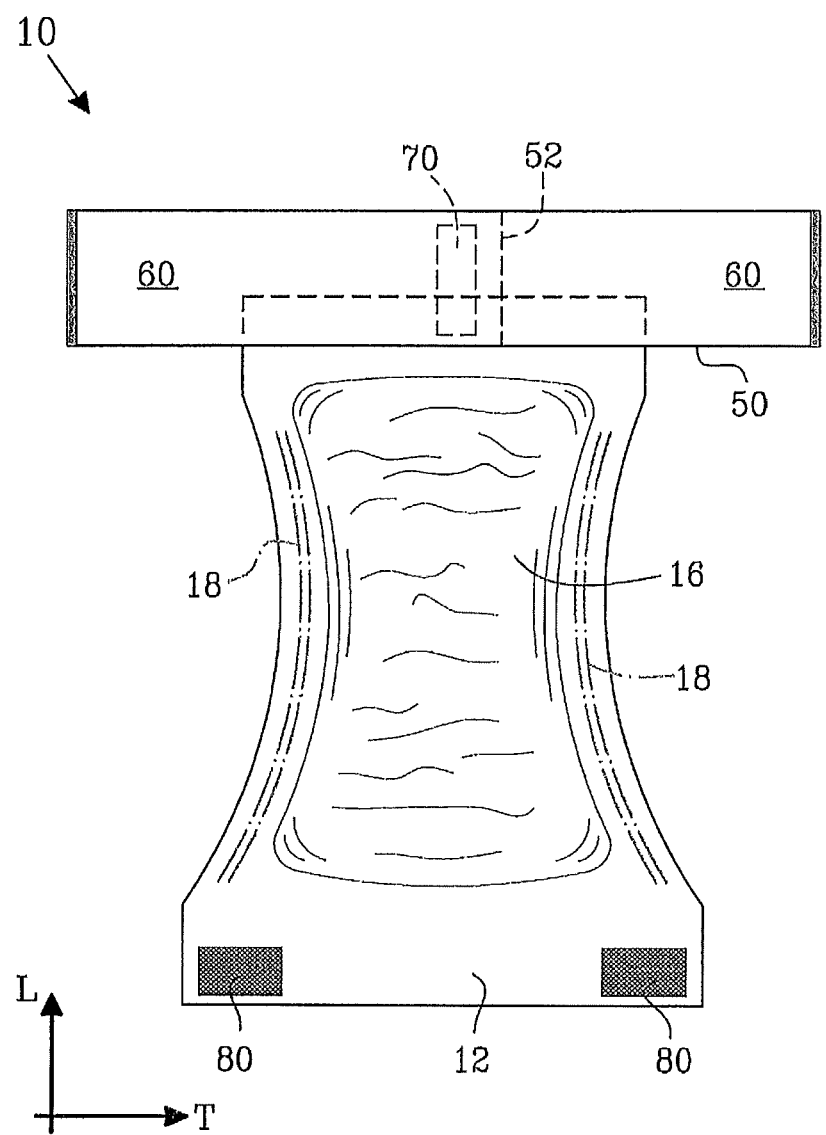

FIG. 1A illustrates an absorbent article 10 according to the invention in the pant diaper form A. In the following description, the first body portion 20 will be referred to as the front portion 20', while the second body portion 30 will be referred to as the rear portion 30'. However, it should be stressed that the reverse arrangement is possible, and the article 10 may be worn the other way round. If this is the case, all references to the "front portion" and "rear portion" in the following text should be reversed.

The article 10 comprises a front portion 20' which in use is located against the stomach of the wearer. In use, a rear portion 30' is located against the lower back/buttocks of the wearer and a crotch portion 40—between said front and rear portions 20', 30' in the longitudinal direction (L) of the article 10—is located between the wearer's legs.

In cross-section, the absorbent article usually comprises a liquid-permeable topsheet 12, a liquid-impermeable backsheet 14 and an absorbent core 16 located between said topsheet 12 and said backsheet 14. However, in certain absorbent articles 10, it is sufficient to include only an absorbent core 16 and a liquid-impermeable backsheet 14.

The topsheet 12 of the article 10 is the layer which lies in contact with the wearer's body when the article is in use. As such, it should be soft, non-irritating and comfortable against the skin, and bodily fluid should be able to pass through it without hindrance. The topsheet 12 can consist of a non-woven material, e.g. spunbond, meltblown, carded, hydroentangled, wetlaid etc. Suitable nonwoven materials can be composed of natural fibers, such as woodpulp or cotton fibres, manmade fibres, such as polyester, polyethylene, polypropylene, viscose etc. or from a mixture of natural and manmade fibres. The topsheet may further be composed of tow fibres, which may be bonded to each other in a bonding pattern, as e.g. disclosed in EP-A-1 035 818. Further examples of materials suitable for topsheets are porous foams, apertured plastic films etc. The topsheet 12 may be different in different parts of the absorbent article 10.

The backsheet 14 of the article 10 is the layer which lies furthest from the wearer's body when the article is in use. To protect the wearer's garments from soiling, it should be liquid-impermeable, but is desirably gas-permeable to allow air and vapour to pass in and out of the article so that the warm, damp conditions which can arise in a diaper are reduced. Typically, the backsheet 14 is of a liquid impervious material, such as a thin plastic film, e.g. a polyethylene or polypropylene film, a nonwoven material coated with a liquid impervious material, a hydrophobic nonwoven material, which resists liquid penetration or a laminate comprising plastic films and nonwoven materials. Examples of breathable backsheet materials are porous polymeric films, nonwoven laminates from spunbond and meltblown layers, laminates from porous polymeric films and nonwovens. The backsheet 14 may be different in different parts of the absorbent article 10.

The absorbent core 16 of the article 10 acts to receive and contain liquid and other bodily exudates and can be of any conventional kind. As such, it typically comprises absorbent material. Examples of commonly-occurring absorbent materials are cellulosic fluff pulp, tissue layers, highly-absorbent polymers (so called superabsorbents), absorbent foam materials, absorbent nonwoven materials or the like. It is common to combine cellulosic fluff pulp with superabsorbents in an absorbent body. It is also common to have absorbent cores comprising layers of different material with different properties with respect to liquid receiving capacity, liquid distribution capacity and storage capacity. The thin absorbent cores, which are common in for example baby diapers and incontinence guards, often comprise a compressed mixed or layered structure of cellulosic fluff pulp and superabsorbent material. The size and absorbent capacity of the absorbent core 16 may be varied to be suited for different uses such as for infants or for incontinent adults.

The absorbent core 16 may comprise one or more layers which are designed to improve the handling of bodily waste. Such layers are designed to receive a large amount of liquid in a short space of time and distribute it evenly across the absorbent core 16. They may include so-called transfer, distribution, surge or acquisition layers, and are usually located between the topsheet 12 and the absorbent core 16.

The topsheet 12 and backsheet 14 generally have a similar extension in the plane of the article, while the absorbent core 16 has an extension which is somewhat smaller. The topsheet 12 and backsheet 14 are joined to one another around the periphery of the absorbent core 16, so that the core 16 is enclosed within the envelope formed by the topsheet 12 and the backsheet 14. The absorbent core 16 is at least located in the crotch portion 40 of the article 10, and may also extend somewhat into the front and rear portions 20',30'. The topsheet 12 and backsheet 14 may be joined to one another by any means common in the art, e.g. ultrasonic welding, thermal welding or gluing.

In addition, the absorbent article 10 may comprise one or more elastic elements 18. These help the article 10 fit tightly against the body of the wearer, and are usually present as leg or waist elastic elements.

The article 10 comprises a waistband 50. The width of the waistband 50 should be between circa 50 mm and 250 mm. The waistband 50 may comprise nonwoven material or plastic film, or laminates thereof. In a preferred embodiment, the waistband comprises a laminate of at least one nonwoven material and at least one plastic film. The waistband 50 may have elastic properties in at least one region thereof, which may be provided by the use of one or more elastic components, such as e.g. elastic threads, elastic nonwoven materials or elastic films. To obtain a more underwear-like appearance, it is preferred that the elastic components are located in the upper edge of the waistband 50 (i.e. that edge which is located furthest from the crotch portion 40 in the pant diaper form A). Elastic properties of the waistband 50 are particularly useful when the article is to be drawn over the hips of the wearer in the pant diaper form A. The waistband is desirably breathable, and the material constituting the waistband may be perforated or porous or the waistband may be spaced from the skin of the wearer by spacer fabric or spacer elements.

In FIG. 1A, the waistband 50 is attached to the front portion 20' and the rear portion 30' of the article 10.

The waistband 50 is preferably permanently attached to the rear portion 30' of the article 10. Permanent attachment of the waistband 50 may be carried out by any means known in the art, e.g. gluing, thermal welding or ultrasonic welding. By "permanent" is meant that it is not intended that the user can detach the waistband 50 from the rear portion 30' of the article without irreversibly destroying the article 10. The waistband 50 is suitably a continuous strip of material(s). The length of the waistband 50 should alone be sufficient to encircle the waist of the wearer.

The front portion 20' of the article 10 is also attached to the waistband 50 in such a way that the lateral edges of the front and rear portions 20', 30' are interconnected by said waistband 50. Thus, the article 10 assumes a pant diaper form (A) in which the waistband 50 forms part of the waist portion of the pant diaper.

The waistband 50 comprises a reception surface 60 for a fastening means. By "reception surface" is meant that at least a part of one face of the waistband 50 is capable of joining to a fastening means. For instance, the reception surface 60 may comprise one component of a hook-and-loop type ("Velcro®") fastener, for instance a loop component, which is usually in the form of a nonwoven material to which the hook material can attach. It may alternatively comprise a plastic surface upon which an adhesive fastener can be attached. Combinations of the above are also possible. Preferably, the reception surface is located on the face of the waistband 50 which faces away from the wearer when in use (i.e. the garment-facing side of the waistband 50). For improved adjustment of fit, the reception surface 60 suitably has a certain extension in the longitudinal direction of the waistband.

The reception surface 60 may constitute the garment-facing surface of the waistband 50 or it may be a separate component which is added to the waistband 50 in a separate manufacturing step. From a manufacturing point of view, it is advantageous if the entire material which constitutes the outer face of the waistband 50 forms a reception surface 60. For example, the entire outer surface of the waistband 50 may comprise loop material (e.g. a nonwoven material) to which a hook element of a hook-and-loop type fastener can be fastened.

The waistband 50 comprises at least one perforation 52, as defined above, which extends across the waistband 50 and allows it to be separated into first and a second belt portions 54, 56. The perforation is suitably arranged substantially in the cross-direction of the waistband, and preferably extends completely across the waistband from one edge to the other. It is preferable that only one perforation is present per waistband. Printed indicia (e.g. figures, lines or characters) may be present on the waistband to indicate the location of the perforation.

Figure 1C:
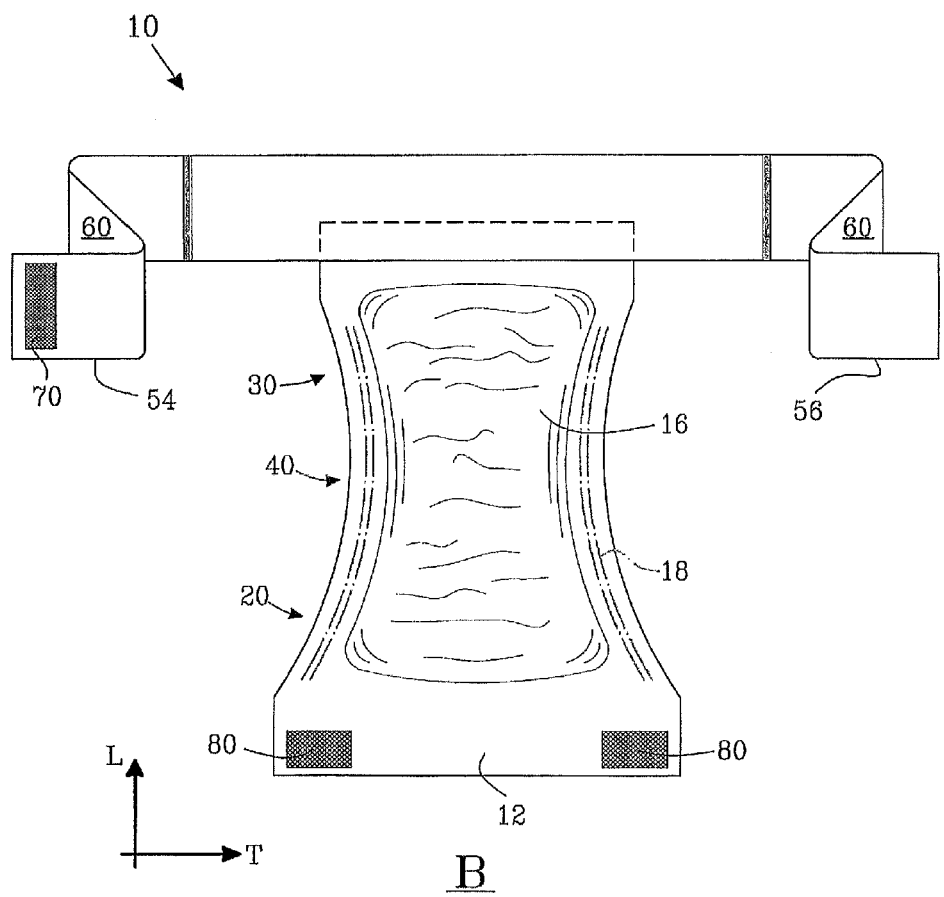

Separating the article 10 at the perforation thus provides a belt diaper form B (FIG. 1C). Each of the belt portions 54, 56 will therefore be attached to the rear portion 30' to which the waistband 50 was attached, as shown in FIG. 1C. The belt portions 54, 56 may be the same length; however, for maximum flexibility in the fit, it is desirable that the second belt portion (the one without the first fastening means 70) is longer than the first belt portion (comprising the first fastening means 70).

Separation of the waistband 50 into two belt portions 54, 56 should allow that—after separation—at least a part of the reception surface 60 is located on each belt portion 54, 56. This is most commonly achieved by the perforation 52 overlapping with reception surface 60 on the waistband 50, such that a single area of reception surface 60 is divided at perforation 52 upon separating the waistband 50. Alternatively, the perforation 52 may be located between two separate areas 60 of reception surface on the waistband 50. In this way, both the first and second fastening means 70, 80 can attach to the reception surface 60 on either or both belt portions 54, 56.

The first belt portion 54 comprises at least one first fastening means 70 adapted to be attached to the reception surface 60 on the second belt portion 56. In this way, the two belt portions 54, 56 can be fastened about the waist of a wearer by attachment of the first fastening means 70 to the reception surface 60. As for the waistband 50 above, the combined length of the two belt portions 54, 56 should be sufficient to encircle the waist of a wearer.

The front body portion of the article 10 (the front portion 20' in the enclosed Figures) comprises at least one second fastening means 80. The second fastening means 80 is adapted to be attached to the reception surface 60 on the first and/or second belt portions, such that the article assumes a belt diaper form B.

In the pant diaper form A, the at least one second fastening means 80 is arranged such that the first body portion (front portion 20') is releasably attached to the reception surface 60 of the waistband 50 via said at least one second fastening means 80. When the article 10 is supplied to the user in the pant-diaper form, the front portion 20' is fastened to the waistband 50 via the second fastening means 80. The word "releasably" is used to mean that the attachment between the second fastening means 80 and the reception surface 60 can be released manually, without requiring force above that which can be applied by a user's hands, without using tools, and without irreversibly destroying one or more components of the article 10.

In other words, the second fastening means 80 is used both in the pant diaper form A to attach the front portion 20' to the waistband 50 via reception surface 60, and in the belt diaper form B to attach the front portion 20' to the belt portions 54, 56 via reception surface 60. This arrangement of the elements of the article 10, in particular the nature and location of the second fastening means 80, allows conversion of the article from the pant diaper form A to the belt diaper form B.

Suitably, the second fastening means 80 is arranged on the wearer-facing side of the front portion 20. Stable diaper structures can be obtained using a single second fastening means 80 which extends along a portion of the width of the front portion 20'. Alternatively, two second fastening means 80 may be arranged at each side edge of the waist region of the front portion 20' (as shown in FIG. 1A), which provides savings in material costs.

Preferably, the first and second fastening means 70, 80 are the same type of fastening means. If the first and second fastening means 70, 80 comprise hook material of a hook-and-loop type fastener, the reception surface 60 should comprise loop material of a hook-and-loop type fastener (e.g. a nonwoven material). If the first and second fastening means 70, 80 comprise adhesive fastening means, the reception surface 60 should comprise reception surface for said adhesive fastening means (e.g. a plastic film).

The sequence illustrated in FIGS. 1A-1E will now be described. They show the actions required to convert an absorbent article of the invention from the pant diaper form (FIG. 1A) to the belt diaper form (FIG. 1C) and apply it to a wearer (FIG. 1E).

The article is supplied in the pant diaper form A (FIG. 1A). In this form, it can be applied to a wearer by being pulled up the legs in the same way as normal underwear.

Figure 1D:
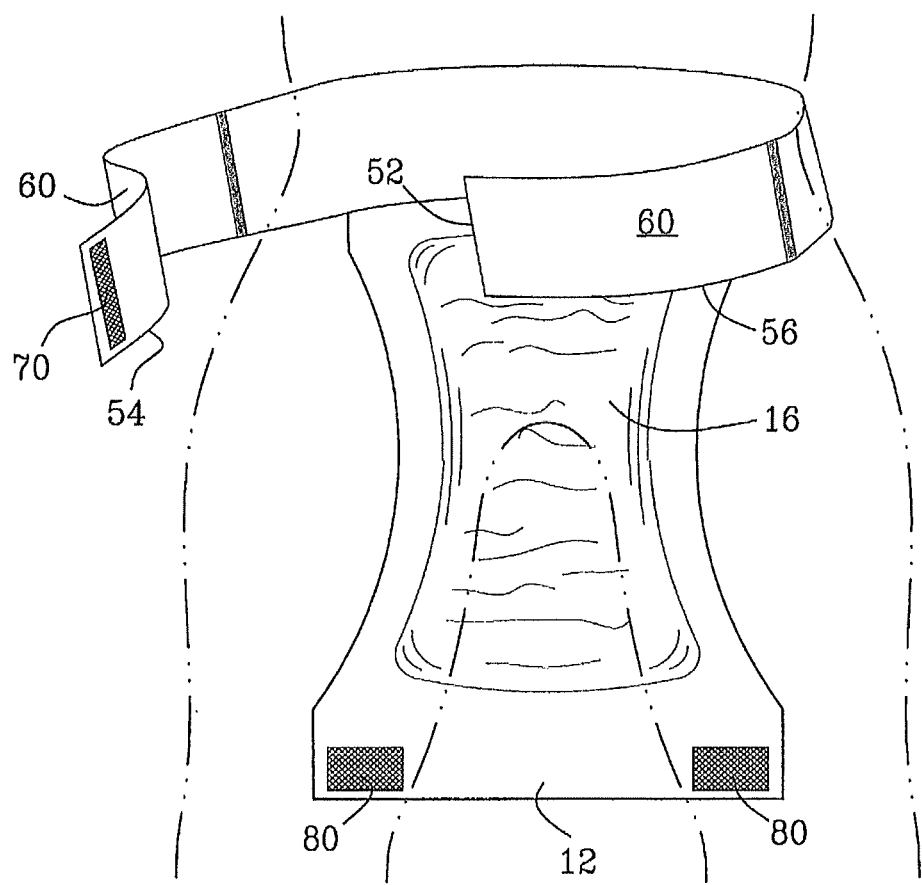
Figure 1E:
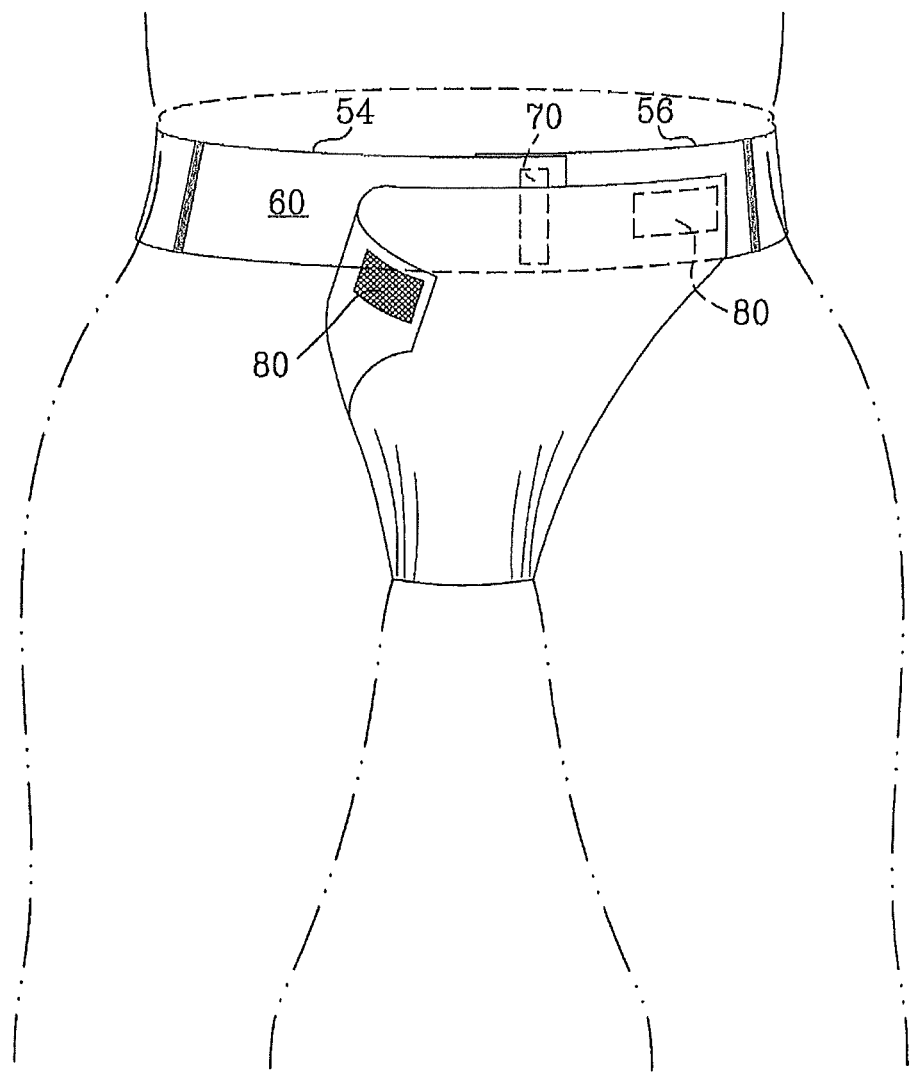

If the article is to be used in the belt diaper form B, the front portion 20' is first detached from the waistband 50 by detaching the second fastening means 80 from the reception surface 60 (FIG. 1E).

The waistband 50 is then separated at perforation 52 into two belt portions 54, 56, as shown in FIG. 1C. It thus has the belt diaper form B.

To apply the belt diaper B to a wearer, the steps illustrated in FIGS. 1D and 1E are taken. The two belt portions 54, 56 are wrapped around the waist of the wearer (illustrated with discontinuous lines in FIGS. 1D-1E) and fastened to each other by attaching the first fastening means 70 on the first belt portion 54 to the reception surface 60 on the second belt portion 56 (FIG. 1D). As shown, when fastening the belt portions around the waist of the wearer, the first belt portion 54 is preferably attached on the outside of second belt portion 56. In this way, the free (unattached) end of the second belt portion 56 does not hang loose, but is tucked between the body of the wearer and the first belt portion 54. However, by use of more than one first fastening means 70 on the first belt portion 54, it may be possible for the first belt portion 54 to be attached to the inside of second belt portion 56.

The front portion 20' of the article 10 is then brought up between the legs of the wearer and fastened to the outside of the belt portions 54,56, by attaching the second fastening means 80 to the reception surface 60 on the first and/or second belt portion (FIG. 1E).

From the above description, it can be understood why it is important that—upon separation of the waistband 50 into two belt portions 54, 56—reception surface 60 is located on both belt portions. In this way, the first fastening means 70 on the first belt portion 54 has corresponding reception surface 60 on the second belt portion 56, while the second fastening means 80 on the front portion 12 has corresponding reception surface 60 on both the first and second belt portions 54, 56. Regardless of the degree of overlap of the belt portions 54,56, provision of reception surface 60 on both belt portions ensures that the second fastening means 80 always has corresponding reception surface 60 to fasten to without compromising the fit or shape of the article 10.

As shown in FIGS. 1A-1E, the second fastening means 80 is suitably arranged such that it is located at least in the edge region of the front portion 20'. In this way, the edges of the front portion 20' are held against the waistband 50 in the pant diaper form A. The second fastening means 80 may comprise two separate second fastening means 80, or a single strip of second fastening means 80 which extends substantially along the waist edge of the front portion 20'.

The location of the reception surface 60 on the belt portions 54, 56 and the waistband 50 depends primarily on the location of the second fastening means 80. It is arranged so that the second fastening means 80 can be joined to the reception surface 60 without compromising the shape or fit of the article 10. If the second fastening means 80 is placed as described above, the reception surface 60 is preferably located at least in the region of the wearer's hips.

Figure 2A:
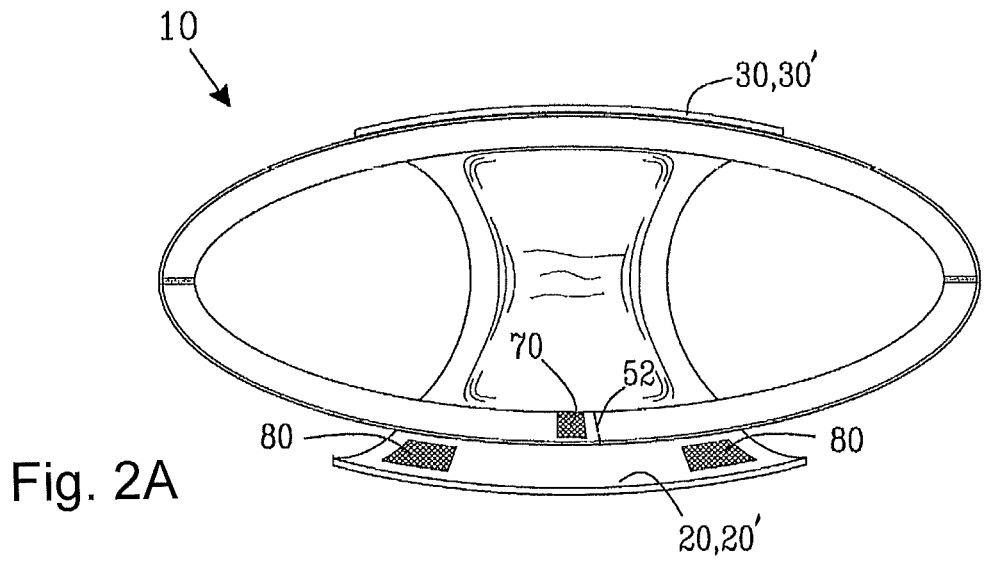
FIGS. 2A-2C, 3A-3C, 4A-4C, and 5A-5C illustrate possible arrangements of the perforation, the second fastening means and the reception surface, as viewed from above.
Figure 2B:
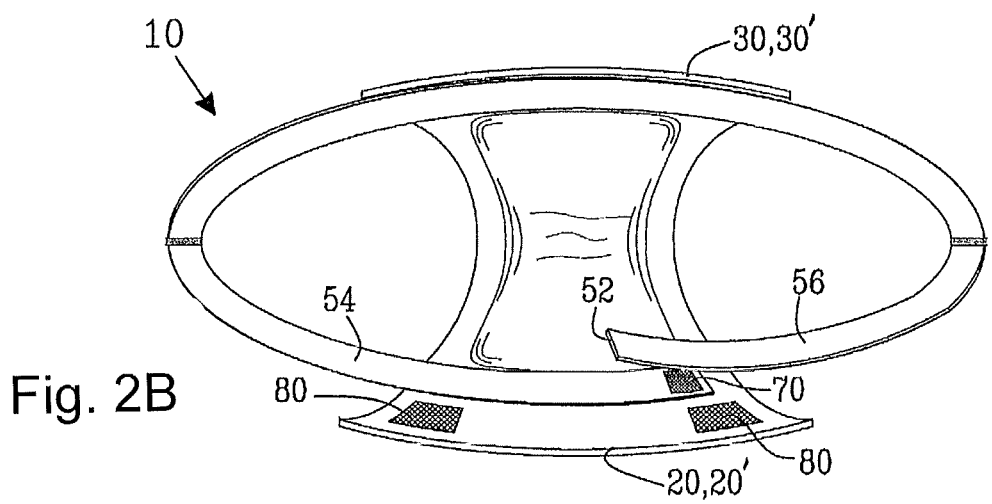
Figure 2C:
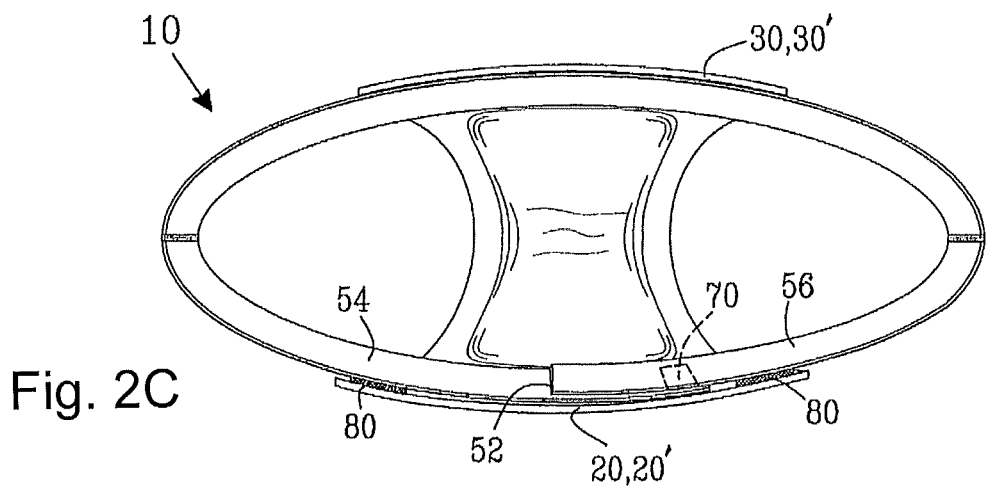

FIGS. 2A-2C show the article of FIGS. 1A-1E from above (plan view), and the sequence used to convert from the pant diaper to the belt diaper form. The front portion 20 is disconnected from the belt 50 (FIG. 2A), the belt is separated at the perforation 52 (FIG. 2B) and the article reassembled in the belt diaper form (FIG. 2C).

Although straightforward, the embodiment of FIGS. 2A-2C can have the disadvantage that the first fastening means 70 contacts the skin of the wearer and can cause damage, irritation and/or discomfort to the wearer's skin. This can be avoided by the first fastening means 70 comprising a softer hook material which is not harsh against the wearer's skin. Alternatively or additionally, a protective layer (not shown) may be placed over the first fastening means 70 which prevents contact between the first fastening means 70 and the wearer's skin, but which can be removed when the first fastening means 70 is to be deployed.

In a preferred embodiment, the first fastening means 70 is arranged to face away from the wearer when the article 10 assumes the pant diaper form A, and is arranged to face towards the wearer when the article 10 assumes the belt diaper form B. This may be achieved in a number of ways, as illustrated in FIGS. 3A-3C and 4A-4C.

Figure 3A:
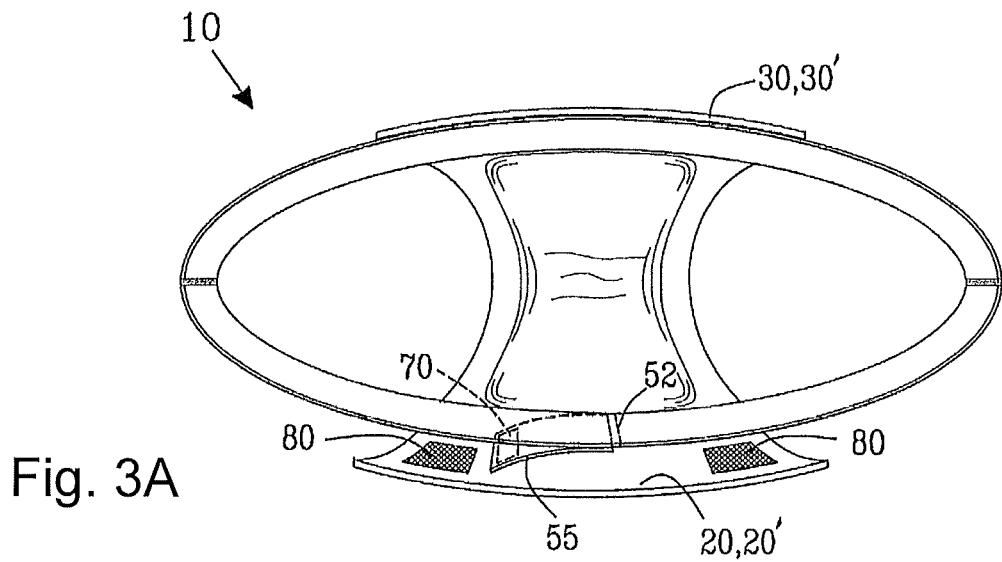

FIG. 3A shows a plan view of the article 10 in the pant diaper form A. As can be seen, the first fastening means 70 is located on a flap 55 on the outside of the waistband 50. The flap 55 is folded so that the first fastening means 70 faces away from the wearer in the pant diaper form A. The flap 55 may be a separate piece of material attached to the waistband 50, or may comprise a section of the waistband material which has been folded over. This embodiment has the advantage that the flap 55 is effectively an extension of the first belt portion 54, allowing for effective overlap of the belt portions in the belt-diaper form, even with no, or little elastic. This embodiment has the additional advantage that the first fastening means 70 can attach to the inside of the front portion 20', providing extra stability to the pant diaper form A.

Figure 3B:
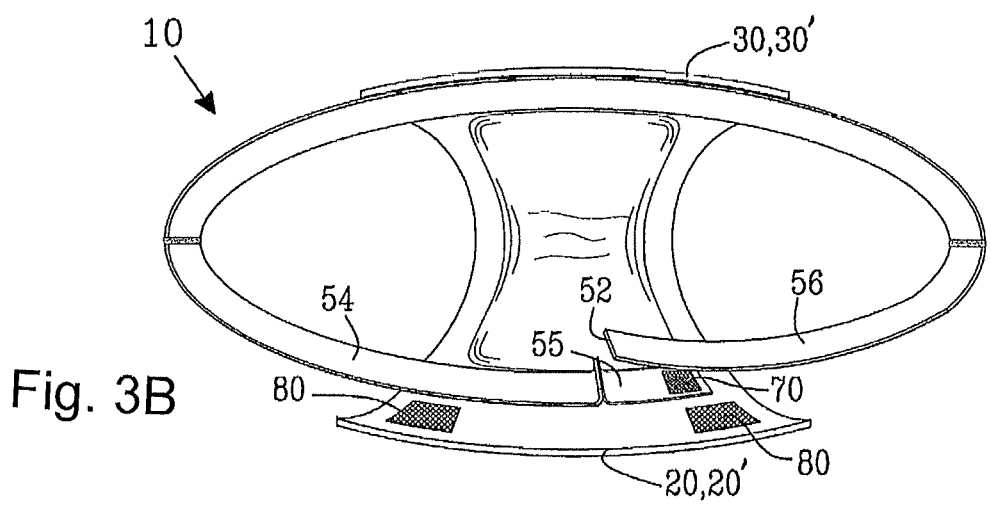
Figure 3C:
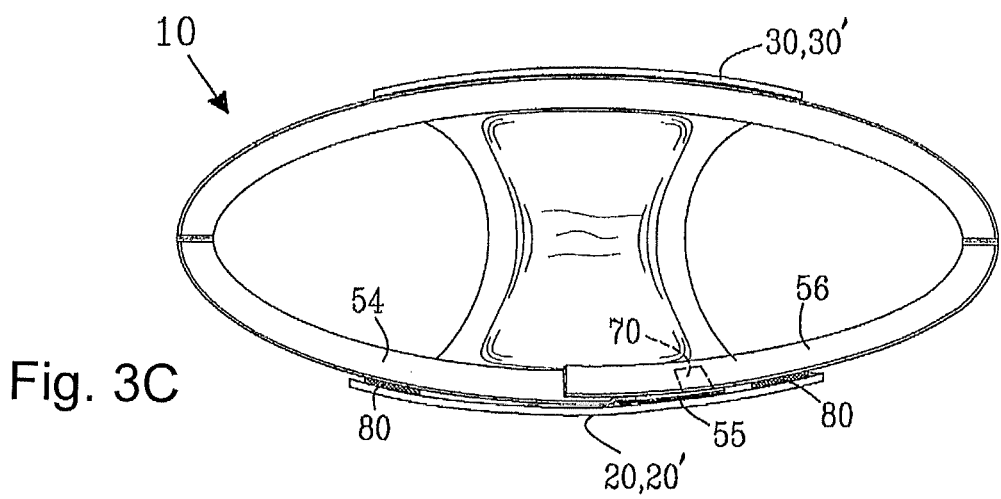

The perforation 52 is located adjacent this flap 55. Upon separation of the waistband 50 into two belt portions, the flap 55 constitutes the free end of the first belt portion 54 (FIG. 3B). It can be folded such that the first fastening means 70 faces towards the wearer in the belt diaper form B (FIG. 3C). It is then in a position to be fastened on the outside of the second belt portion 56, which prevents the free end of the second belt portion 56 from hanging loose, as described above.

Figure 4A:
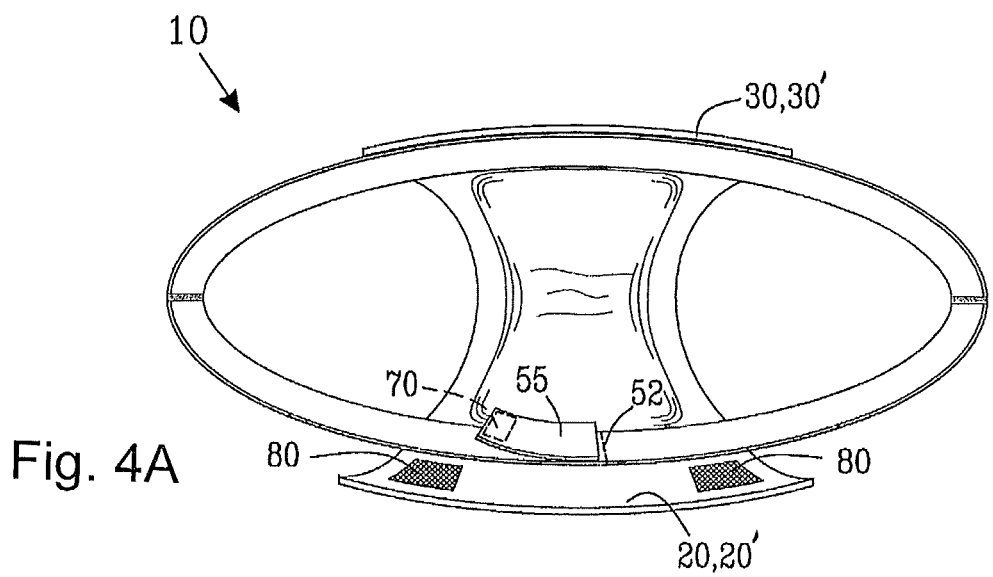

Alternatively, flap 55 is located on the inside of the waistband 50 in the pant diaper form A, and is folded over so that the first fastening means 70 faces away from the wearer in the pant diaper form A (FIG. 4A). Such an arrangement prevents the rough or adhesive surface of the first fastening means 70 from coming into contact with the wearer, thus avoiding damage, irritation and/or discomfort to the wearer's skin.

Figure 4B:
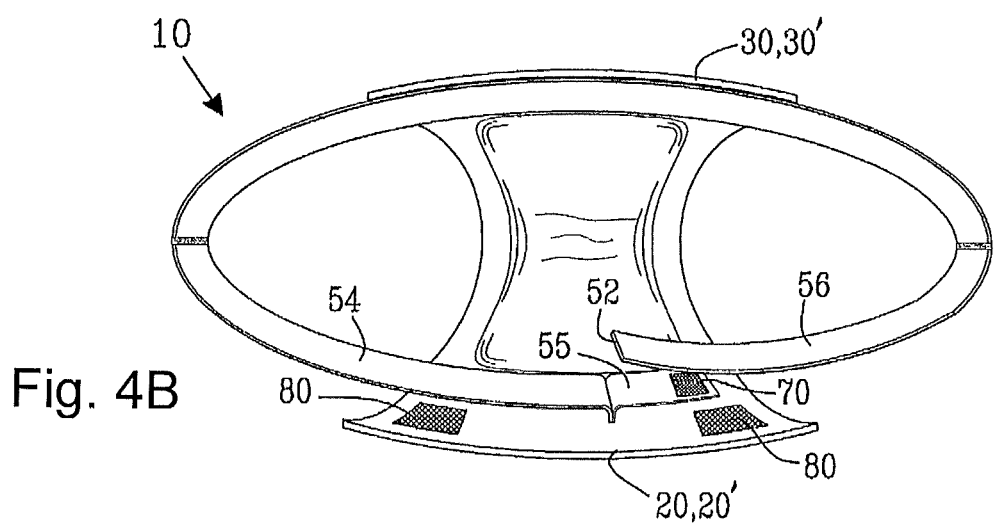
Figure 4C:
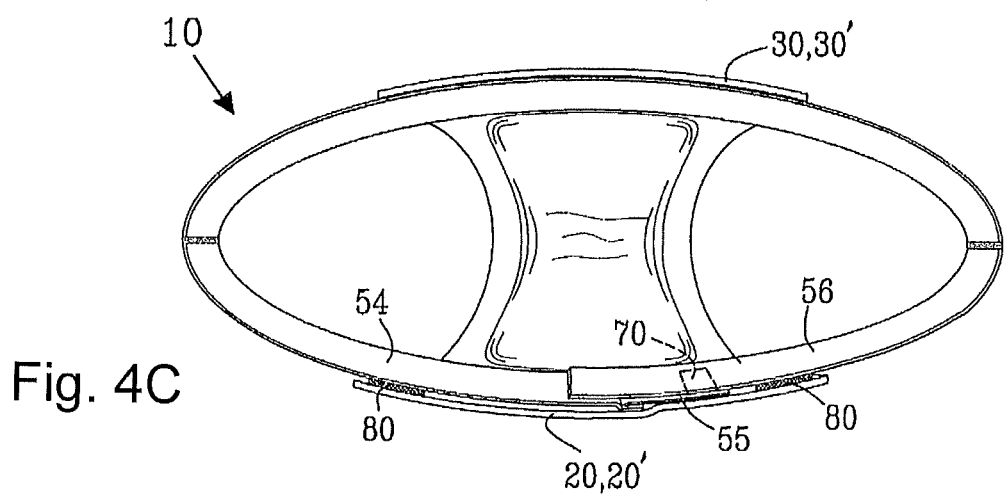

When the waistband 50 is separated at the perforation, the flap 55 again forms the free end of the first belt portion 54 (FIG. 4B). It is then folded out so that the first fastening means 70 faces towards the wearer in the belt diaper form B (FIG. 4C). It is then in a position to be fastened on the outside of the second belt portion 56, as described above with respect to FIG. 2C. An additional advantage is that the joint formed between the flap 55 and the first belt portion does not press against the wearer in the belt-diaper form B.

Figure 5A:
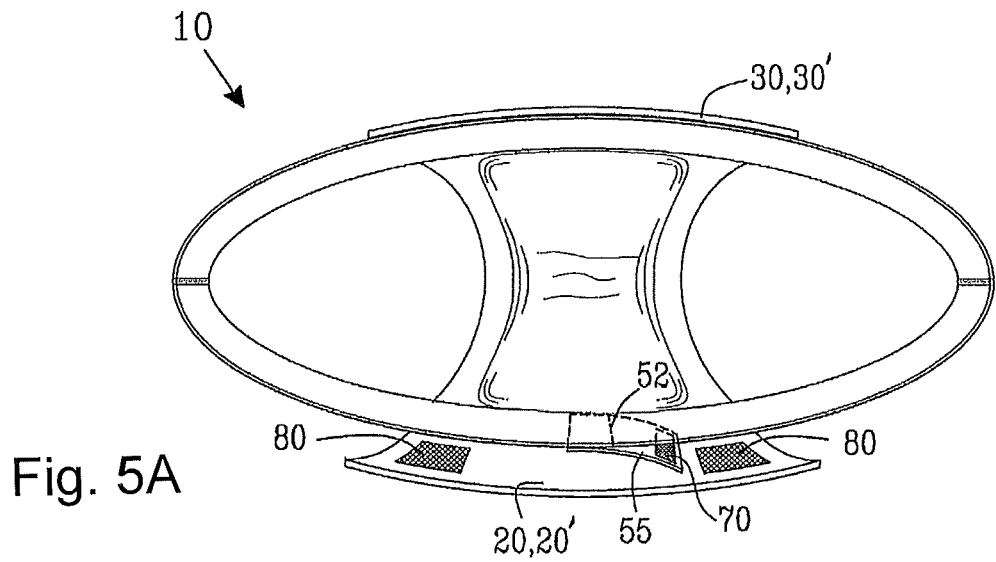
Figure 5B:
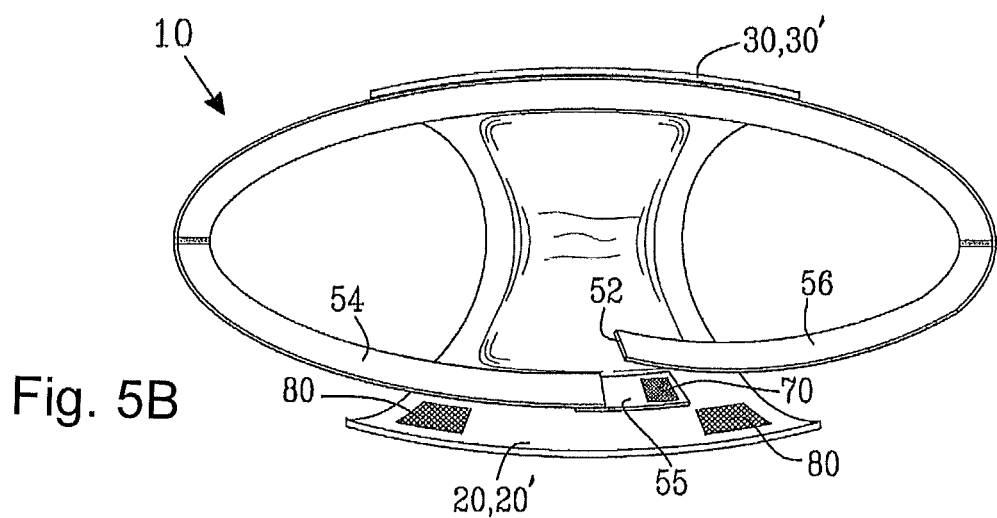
Figure 5C:
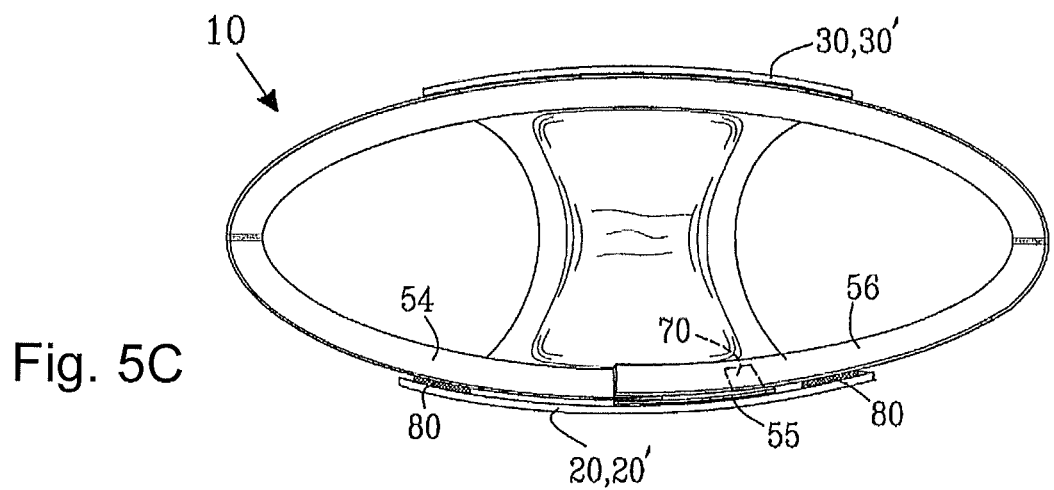

Another embodiment is shown in FIGS. 5A-5C. This embodiment includes a flap 55 located such that the flap 55 overlaps the perforation 52. The first fastening means 70 is arranged on the inside (wearer-facing side) of the flap 55 in the pant-diaper form A (FIG. 5A). Separation of the waistband 50 into first and second belt portions 54, 56 allows the flap 55 to be deployed to overlap the first belt portion 54 over the second belt portion 56 (FIG. 5B). The first fastening means 70 can then be fastened to the reception surface 60 on the outside of the second belt portion 56 in the belt-diaper form B (FIG. 5C).

Preferably, the first fastening means 70 is located adjacent to the free end of the first belt portion 54 formed upon separating the waistband 50. By "adjacent to" is meant that the first fastening means 70 is located in the vicinity of e.g. within 5 cm, preferably within 2 cm, more preferably within 1 cm of the free end of the first belt portion 54, as measured in the longitudinal extension first belt portion 54. In such a way, the material of the waistband 50 is fully utilised when separated into two belt portions 54, 56.

FIG. 6 illustrates a method for manufacturing the absorbent articles 10 according to the invention. As above, the method will be described with reference to a front portion 120' which corresponds to the first body portion 120, and a rear portion 130' which corresponds to the second body portion 130. However, it should again be stressed that the reverse arrangement is possible, and the article 10 may be produced the other way round. If this is the case, all references to the "front portion" and "rear portion" in the following text should be reversed To begin with, first and second continuous parallel webs of waistband material 150, 150' are provided. At least the first web of waistband material 150 comprises a reception surface 160, although it may be desirable for greater flexibility of fit that both webs 150, 150' comprise reception surface 160 for a fastening means. The first web of waistband material 150 is provided with perforations 152 at a predetermined spacing. This web 150 is also provided with first fastening means 170 at the same predetermined spacing. The first fastening means 170 may be applied directly to the first web 150, or via a flap 155 (not shown) which comprises the first fastening means 170 at one end thereof and which is attached to the first web 150 at the other end thereof.

Chassis elements 115 having a front portion 120', a rear portion 130' and a crotch portion 140 are also provided. The chassis elements 115 further comprise at least one second fastening means 180 on the front portion 120' thereof. The chassis elements 115 suitably comprise a liquid-permeable topsheet 12, a liquid-impermeable backsheet 14 and an absorbent core 16, as described above.

Chassis elements 115 can be manufactured as follows: a continuous web of topsheet 12 material is provided, and absorbent cores 16 are placed on this web at regular intervals. A continuous web of backsheet 14 material is laid over the absorbent cores 16, so that the cores 16 are sandwiched between the topsheet 12 and backsheet 14 materials. The topsheet 12 and backsheet 14 materials are then joined to one another by any suitable method. Second fastening means 180 are applied to the chassis element 115 in the front 120' or rear 130' portion thereof (usually to the liquid-permeable topsheet 12) at the same regular intervals as the absorbent cores 16. The individual chassis elements with associated absorbent core 16 and second fastening means 180 are then separated by cutting through the webs of backsheet 14 and topsheet 12 material. If required, leg cuts can also be made at this point. Of course, the chassis elements 115 can also be manufactured the opposite way, with absorbent cores 16 first being placed on a continuous web of backsheet 14 material and being overlaid by a continuous web of topsheet 12 material. Elastic elements may be provided in the leg opening areas and/or in the waist areas.

The chassis elements 115 are placed on the webs of waistband material 150,150' at the same predetermined spacing as that between adjacent perforations 152 and that between adjacent first fastening means 170. The chassis elements 115 are placed so that the at least one second fastening means 180 on the front portion 120' of each chassis element 115 overlaps with the first web of waistband material 150. The rear portion 130' of each chassis element 115 (without second fastening means 180) overlaps with the second web of waistband material 150'. For ease of manufacture, the chassis 115 is usually placed so that the topsheet 12 is in contact with the first and second webs of waistband material 150,150' in both the front 120' and rear 130' portions of the chassis 115. However, it may be conceivable that in the chassis 115 is placed so that, in the rear portion 130', it is the backsheet 14 which contacts the second web of waistband material 150'.

The rear portion 130' of each chassis element 115 is attached (preferably permanently attached) to the second web of waistband material 150'. Attachment of the second web of waistband material 150' may be achieved by any means known in the art, e.g. adhesion, sewing or thermal or ultrasonic welding.

The second fastening means 180 of the front portion 120', is attached to the first web of waistband material 150. Hence, the front portion 120' is releasably attached to the reception surface 60 on said first web of waistband material 150.

Each chassis element 115 is then folded in the crotch portion 140 such that the first and second webs of waistband material 150, 150' are brought into contact in the region between the chassis elements 115. Normally, this contact between the first and second webs 150,150' will be face-to-face. The folding is such that the liquid-impermeable backsheet 14 is located on the outside of the article 10, while the topsheet 12 is located on the inside.

The first and second webs of waistband material 150, 150' are then joined to each other at the same predetermined spacing, in the region between the chassis elements 115. Joining may be effected by any means known in the art, e.g. adhesion or thermal or ultrasonic welding.

After being joined to one another, the first and second webs of waistband material 150,150' are then cut at the predetermined spacing in such a way that they remain joined to each other on both sides of each cut. For example, a cut could be made within a joined region, leaving joined webs on each side of the cut. Alternatively, there a join may be located immediately on either side of the each cut.

The first and second webs of waistband material 150, 150' are cut in such a way that the length of waistband material 150,150' between each cut includes a chassis element 115, a perforation 152 and a first fastening means 170, as shown in FIGS. 5A-5C. In this way, individual absorbent articles 10 are provided.

The method described herein may include one or more steps which provide one or more of the preferred features of article 10 described above. For instance, additional components of the absorbent article, such as elastic elements 18 may be introduced to the webs of waistband material 150,150' or to the chassis element 115 before or after the above-described steps. Additionally, the first fastening means 170 may be located on a flap as described for the embodiments of FIGS. 3A-3C, 4A-4C, and 5A-5C.

Preferably, in the manufacturing method, the perforation 152 is located adjacent the first fastening means 170, wherein "adjacent" has the same meaning as described above.

The absorbent article of the present invention offers the user a choice as to whether it should be applied in the pant diaper form A, or the belt diaper form B. For simplicity and for rapid change of a soiled diaper, a user might choose to use the pant diaper form A. However, belt diapers can be adjusted to fit a wider range of waist sizes than pant diapers, as the overlap of the first and second belt portions can be adjusted as desired. For improved fit, therefore, a user might choose to use the belt diaper form B.

In addition, absorbent articles which can assume more than one form provide advantages in material costs and manufacturing, as the design can be optimised to minimize usage of expensive components. For instance, the fact that a belt diaper usually fits a wider range of waist sizes than a pant diaper means that good fit of the article can be obtained without necessarily providing the entire waistband 50 of the pant diaper with elastic means.

Although the present invention is illustrated with reference to a diaper, the invention should not be considered limited to such articles. In particular, the invention should be considered as including incontinence articles which can be converted from a pant form to a belt form. In addition, features of the absorbent article described in various embodiments may be combined with each other, yet remain within the scope of the present invention. Although the invention has been described with respect to the above embodiments, the invention for which protection is sought is defined by the appended claims.

The invention claimed is:

1. An absorbent article comprising a first body portion, a second body portion and a crotch portion located between said first and second body portions in a longitudinal direction of the article;

the article comprising a waistband which is attached to the second body portion of the article such that the lateral edges of the second body portion are interconnected by said waistband, said waistband including a reception surface for a fastener, the reception surface facing away from a wearer when the article is being worn;

said waistband comprising at least one perforation extending across the waistband which allows the waistband to be separated into first and second belt portions, whereby at least a part of the reception surface is located on each belt portion;

wherein the first belt portion comprises a foldable flap, the foldable flap being connected to the first belt portion at a connection region on the first belt portion adjacent the perforation, the foldable flap including at least one first fastener on one surface of the foldable flap;

the first body portion of the article comprising at least one second fastener adapted to be attached to the reception surface on the first and/or or second belt portion, said at least one second fastener is arranged such that the first body portion is releasably attached to the reception surface of the waistband via said at least one second fastener;

wherein when the first and second belt portions are integrally connected to each other at the perforation, the foldable flap lies flat against a wearer-facing surface of the first belt portion such that the first fastener faces the first body portion when the first body portion is releasably attached to the reception surface of the waistband and the article is worn as a pant diaper; and when the first and second belt portions are separated from each other at the perforation, the foldable flap is adaptable to lie such that the first fastener faces the reception surface of the second belt portion and fastens the foldable flap to the second belt portion when the article is worn as a belted diaper.

2. The article according to claim 1, wherein the reception surface constitutes a garment-facing surface of the waistband.

3. The article according to claim 1, wherein the first and second fasteners comprise hook material of a hook-and-loop type fastener and the reception surface comprises loop material of a hook-and-loop type fastener.

4. The article according to claim 1, wherein the first and second fasteners comprise adhesive fastening means and the reception surface comprises a reception surface for said adhesive fastening means.

5. The article according to claim 1, wherein the perforation is located adjacent or aligned with a longitudinal center line of the first body portion.

6. The article according to claim 1, wherein the waistband has elastic properties in at least one region thereof.

7. A method for manufacturing the absorbent article of claim 1, said method comprising the steps of:
providing first and second continuous parallel webs of waistband material; at least the first web of waistband material comprising a reception surface for a fastener, the first web of waistband material being provided with perforations at a predetermined spacing in at least a portion of the first web in which said reception surface is present;

providing chassis elements having a first body portion, a second body portion and a crotch portion; said chassis elements further comprising at least one second fastener on the first body portion;

placing the chassis elements on the webs of waistband material at the predetermined spacing, so that the at least second fastener on the first body portion of each chassis element overlaps with the first web of waistband material, and the second body portion of each chassis element overlaps with the second web of waistband material;

attaching the second fastener of the first body portion to the first web of waistband material; and attaching the second body portion of each chassis element to the second web of waistband material;

folding each chassis element in the crotch portion such that the first and second webs of waistband material are brought into contact in the region between the chassis elements;

joining the first and second webs of waistband material to each other at the predetermined spacing, in the region between the chassis elements;

cutting the first and second webs of waistband material at the predetermined spacing in such a way that the first and second webs of waistband material remain joined to each other on both sides of each cut, and in such a way that the length of waistband material between each cut includes a chassis element, a perforation and a first fastener; so as to provide individual absorbent articles.

8. An absorbent article comprising:
a first body portion, a second body portion and a crotch portion located between said first and second body portions in a longitudinal direction of the article;

a waistband which is permanently attached to the second body portion of the article such that detachment of the waistband from the second body portion will cause irreversible destruction of the article;

the waistband comprising a single length of material;

said waistband comprising a first reception surface for a fastener and a second reception surface for a fastener, said reception surfaces located on surfaces facing away from a wearer of the absorbent article;

said waistband comprising at least one line of weakness extending across the waistband which allows the waistband to be separated into first and second belt portions, the line of weakness being arranged between the first and second reception surfaces whereby at least one reception surface is located on each belt portion when the waistband is separated at the line of weakness into first and second belt portions;

wherein the first belt portion comprises a foldable flap, the foldable flap being connected to the first belt portion at a connection region on the first belt portion adjacent the line of weakness, the foldable flap including at least one first fastener on one surface of the foldable flap;

the first body portion of the article comprising at least one second fastener adapted to be attached to the first or the second reception surface on the first or second belt portion;

said at least one second fastener is constructed such that the first body portion is releasably attached to the reception surface of the waistband via said at least one second fastener such that the second fastener can be released and refastened without damaging the second fastener or the reception surface;

wherein when the first and second belt portions are integrally connected to each other at the line of weakness, the foldable flap lies flat against a wearer-facing surface of the first belt portion such that the first fastener faces the first body portion when the first body portion is releasably attached to the reception surface of the waistband and the article is worn as a pant diaper; and when the first and second belt portions are separated from each other at the line of weakness, the foldable flap is adaptable to lie such that the first fastener faces the reception surface of the second belt portion and fastens the foldable flap to the second belt portion and the article is worn as a belted diaper.

\* \* \* \* \*